United States Patent [19]
Mentovay et al.

[11] 4,093,902
[45] June 6, 1978

[54] HIGH SENSITIVITY ELECTRONIC INTEGRATING TORQUE RHEOMETER

[76] Inventors: Leonard W. Mentovay, 16 Fairmount Rd., Parsippany, N.J. 08859; Alex Palmer, 24 Westwood Dr., Fair Lawn, N.J. 07410

[21] Appl. No.: 755,359

[22] Filed: Dec. 29, 1976

[51] Int. Cl.² ............................................. G05B 1/08
[52] U.S. Cl. .................................................. 318/490
[58] Field of Search ............... 318/490, 432, 433, 434, 318/445

[56] References Cited
U.S. PATENT DOCUMENTS

| | | | |
|---|---|---|---|
| 3,909,692 | 9/1975 | Jungel | 318/490 |
| 3,951,389 | /1976 | Porter | 366/441 |

*Primary Examiner*—Herman J. Hohauser
*Attorney, Agent, or Firm*—Siegmar Silber

[57] ABSTRACT

A mixing control system for elastomeric materials is described that includes a mixer housing forming a mixing chamber therein for receiving said elastomeric materials; at least one rotatable mixing means in the chamber; a dynamometer coupled to and driving said rotatable mixing means; torque sensing means for detecting torque exerted by the mixing means; said sensing means providing a torque signal level for controlling said mixing means; voltage-to-frequency conversion means for processing signal in which the pulse frequency varies in correspondence to the amplitude of the signal level; pulse counting means for continuously and cumulatively counting the pulses of said pulse signal; display means for displaying the count of said pulse counting means as the value of the integral of said signal level with respect to time; and control responsive means automatically responsive to a predetermined integrated value of said display means for controlling the total mixing energy input to the mixing control system.

15 Claims, 8 Drawing Figures

HIGH SENSITIVITY ELECTRONIC INTEGRATING TORQUE RHEOMETER

BACKGROUND OF THE INVENTION

1. Field of the Invention

The present invention relates to metrication of machine torque characteristics and the electronic integration thereof, and more particularly for determination of work input to production machinery, especially in the plastics compounding and food mixing processes.

2. Description of the Prior Art

In the past, work expended in mixing has been measured by integration with respect to time of the electrical power utilized in operating production machinery and thereby derive an estimate of shaft horsepower. Typical of this approach is the U.S. Pat. 3,951,389, issued Apr. 20, 1976 to John P. Porter and entitled, "Elastomer Processing Method." The Porter patent teaches monitoring electrical power consumed by an elastomer processing apparatus under load conditions, compensating the quantum obtained by reducing the same by the amount under no-load conditions to arrive at a net power consumed for process work, converting the net power consumed to an electrical signal, and then integrating the signal with respect to time to provide an output for control purposes. However, a device for determining the integral of mixer to torque with respect to time is not within the teaching of Porter. At present laboratory models of torque rheometers are used throughout the polymer processing industry as quality control and research instruments. Torque rheometers provide a continuous readout and/or recording of torque during mixing and can be equipped with various high shear mixing heads or extruders to simulate specific production processes. The torque rheometer provides the formulator, processor and end user with the means to derive information needed to assure processing uniformity from batch to batch and guard against reject and waste. In the case of plastics and elastomers, for example, it is vital to understand how a given formulation reacts to specific production equipment and processing conditions. The torque temperature data obtained from laboratory torque rheometers is related to polymer processing characteristics and can be used only as a relative measure. Torque temperature data alone does not provide a measure of work input. Work input measurements have been shown to provide an accurate means of controlling processes to reach optimum properties. For example, overmixing polymeric compounds can result in polymer degradation and wasted energy; and undermixing can result in improper dispersion causing poor physical properties.

Recently much research has been done in the area of predicting general processing characteristics polyvinyl chloride (PVC) such as dynamic thermal stability, melt flow properties, and fusion and melting aspects of PVC compounds. Recent studies such as that of Pravin L. Shah entitled "Predicting PVC Extrudability from Melt Temperatures," *SPE Journal*, Vol. 29, No. 4, April 1973, have been published. Shah found that the Brabender Plastograph can be used to predict extrudability of PVC compounds. Significantly, from a practical standpoint, the method did not require conversion of Brabender data into formal rheological units. Furthermore, data derived from this rheometry technique provides better understanding of the parameters useful in predicting extrudability. Finally, there was found to be an interesting byproduct of this viscometry concept, namely, the characterization of external and internal lubricants from the standpoints of viscosity reduction and frictional heat generation. Further, the researcher found on a theoretical level that the area under the torque curve from the Brabender Plastic-Corder recorder had wide application in that various critically important rheometric developments could be monitored. The rheometric data thus produced was comparable to those employing more formal techniques and that the torque rheometry was pragmatically sound. Since that time, further application data for integrated torque curves has developed. While mechanical and electronic planimetry devices currently on the market were examined for this application, none exhibited the sensitivity required. Thus, there arose a need for a versatile integration system to meet the needs of present-day plastics technology through measurement of torque and subsequent integration of torque curves.

SUMMARY OF THE INVENTION

The subject invention pertains in general to a mixing control system for elastomeric materials that controls mixing by determining the amount of torque expended by the mixing means.

More particularly and in accordance with the invention a mixing control system for elastomeric materials is provided that includes, a mixer housing forming a mixing chamber therein for receiving the elastomeric material; at least one rotatable mixing means in the chamber; a dynamometer coupled to and driving said rotatable mixing means; torque sensing means for detecting torque exerted by the mixing means; said sensing means providing a torque signal level for controlling said mixing means voltage-to-frequency conversion means for processing said signal level and for converting said signal level into a pulse signal in which the pulse frequency varies in correspondence to the amplitude of the signal level; pulse counting means for continuously and cumulatively counting the pulses of said pulse signal; display means for displaying the count of said pulse counting means as the value of the integral of said signal level with respect to time; and, control responsive means automatically responsive to a predetermined integrated value of said display means for controlling the total mixing energy input to the mixing control system.

It is an object of this invention to provide control means by quantitatively characterizing the torque with respect to time required for mixing of elastomeric melts.

It is a further object of the present invention to provide a control instrument of high sensitivity responsive to an integrated value of an analog signal representative of processing torque.

It is a yet further object of the present invention to provide an integrator for use with known torque rheometers.

It is a feature of the present invention to optimize mixing process work by providing the proper total energy to mix sufficiently without overworking the medium and thereby maintaining melt homogencity.

Other objects, as well as various features of the invention, appear hereinafter wherein a system for mixing control is disclosed. This disclosure of the invention will be more fully appreciated when taken in conjunction with the accompanying detailed descriptions of preferred embodiments and the attached drawings.

BRIEF DESCRIPTION OF THE DRAWINGS

This invention is described with reference to the accompanying drawings in which.

DETAILED DESCRIPTION OF THE PREFERRED EMBODIMENT

Figure 1:
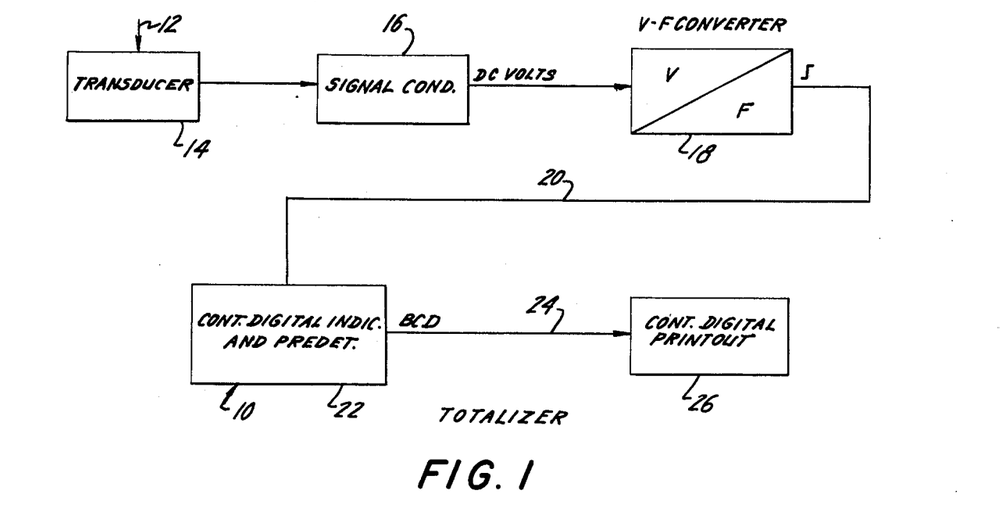
FIG. 1 is a schematic illustration of the high sensitivity electronic integrating torque rheometer of the present invention.

The measurement and integration of mixing torque is shown schematically in the system block diagram of FIG. 1. In FIG. 1, the torque integrator 10 is shown in block form for exemplary purposes. The d-c voltage input 12 is derived from TRANSDUCER unit 14 by way of SIGNAL COND. (conditioning) unit 16. The transducing element suitable for the above application may be either of the existing torque rheometers, namely, the mechanical or electronic Plasti-Corder ® instruments (available from C. W. Brabender Instruments, Inc., South Hackensack, N.J. 07606). The input signal 12 is proportional to absolute torque and the maximum value is determined by the horsepower range of the torque rheometer. In block 18, labeled VARIABLE RATE, the d-c voltage is converted by a voltage-to-frequency converter of the high-impedance type that generates square-wave pulses in direct proportion to the d-c level input. The pulse output 20 is provided as an input for the PULSE COUNTER unit 22 which continuously displays and accumulates the pulses generated. The counter is arranged to provide a binary coded decimal output 24 (labeled BCD) to the printer 26 which at preselected time intervals, interrogates the display and prints out the achieved integration level.

During printout the integration process continues uninterrupted even though the print display is of a instantaneously achieved or frozen value. Thus, no loss in integrated value results, since the counter memory accumulates data transmitted while the display is frozen and interrogated. The displayed value automatically updates when the counter is switched back into the count mode. Switching in and out of memory mode and providing a printed command signal is achieved by a precision timer. The counter incorporates a comparator network and predetermination selector switch. This closes a relay when a preselected value has been reached and automatically stops the torque rheometer drive at a precise level of work input. The printed digital data obtained from the printer provides an absolute measure and permanent record of the torque-time integral. This data can be converted to work input values in whatever engineering units are desired.

Figure 2:
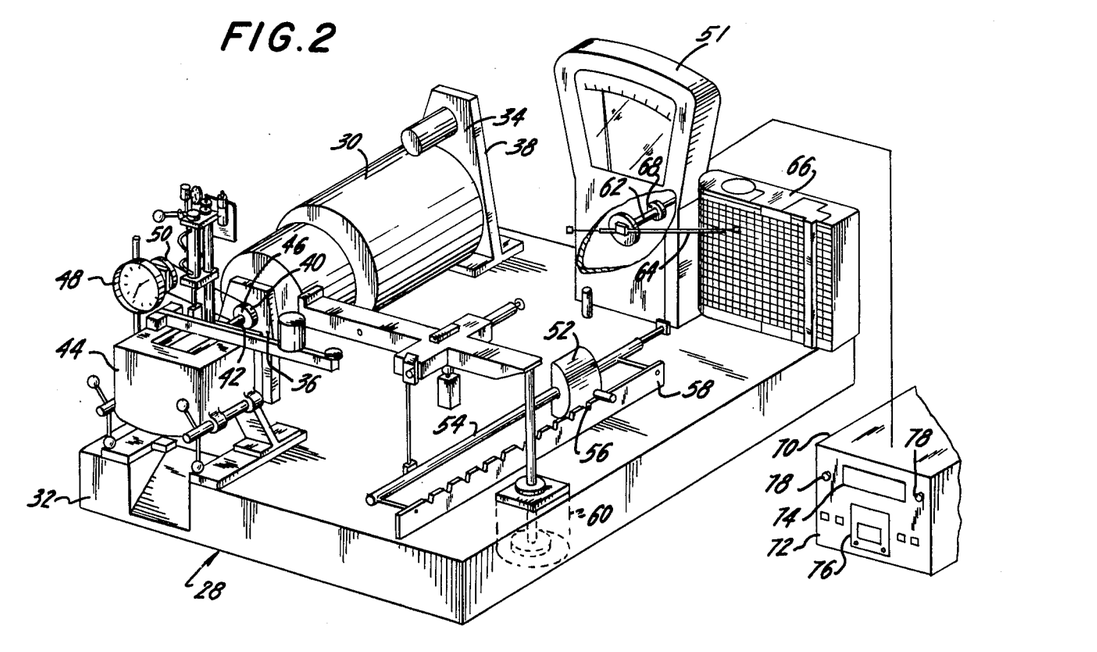
FIG. 2 is a perspective view showing the mechanical elements used to measure mixing torque for the mechanical version of the first embodiment of the invention of FIG. 1.

Referring now to FIG. 2, a first embodiment of the present invention is shown. This embodiment employs a mechanical torque rheometer 28 that is structured to include a dynamometer or drive 30 mounted on a base plate 32. The mounting arrangement provides for bearing housings 34 and 36 for retaining precision bearings 38 and 40, respectively. The precision bearing 38 accomodates one end of shaft 42 and the opposite end extends through bearing 40 for coupling to a driven unit 44. Medial to bearing 40 and driven unit 44 is mounted a tachometer takeoff 46 connected in turn to tachometer 48 through pulley 50. The driven unit or measuring head 44 is discussed in further detail below. The most commonly employed measuring head is a miniature batch mixer 46 utilizing the rotary power from dynamometer 30. Upon providing an output to the measuring head 44, a torque is experienced depending upon the materials being mixed, the time elapsed in the mixing cycle and numerous other factors including, but not limited to, mixer geometry. The torque rheometer 28 is provided with a balance beam and damped level arrangement 50 for providing a mechanical torque (or strain) input to scale indicator 51. The scale zero is suppressed through a structure providing a counterbalancing weight 52 slidable along beam 54 to any one of several detented stops 56 or coupling positions on stop bar 58. The lever arrangement 50 is provided with oil dashpot 60 that slows the rate of movement and oscillation of the mechanical linkage to the scale indicator. In the unit shown the indicator movement 62 is structured to provide movement for a pen arm 64 of a strip-chart recorder 66. Additionally, the indicator movement 62 is linked to potentiometer 68 for providing input to integrator unit 70. The panel 72 of integrator includes a digital readout meter 74 and a digital printer 76 for displaying integrated values. The panel also includes the normal control features and selector switches 78 for matching integrator range to that of scale indicator 51 where selector positions correspond to detented stops 56, described above.

While the integration means of this invention is applicable to production process equipment, including batch mixers, the embodiment described herein describes the invention as applied to laboratory scale mixer. The measuring head of the laboratory scale mixer is referred to generally as reference designator 80. The measuring head is shown in detail in FIG. 3. The measuring head is supported on a stand 82 with bowl support studs 84 attached thereto. Adjacent the studs is positioned mixing bowl backplate 86 upon which is mounted Banbury ® type (Banbury is a registered tradename of the Farrel Corp.) blades 88 for mechanical coupling with dynamometer output shaft 42. The studs 84 are adapted to receive removable mixing bowl 90 which in turn are affixed thereto by spin-tight fasteners 92. Both the bowl 90 and the bowl backplate 86 are constructed to form a temperature-controlled, jacketed housing that include thermal liquid inlet/outlet ports 94 so as to simulate closely full-scale elastomeric mixers.

Figure 3:
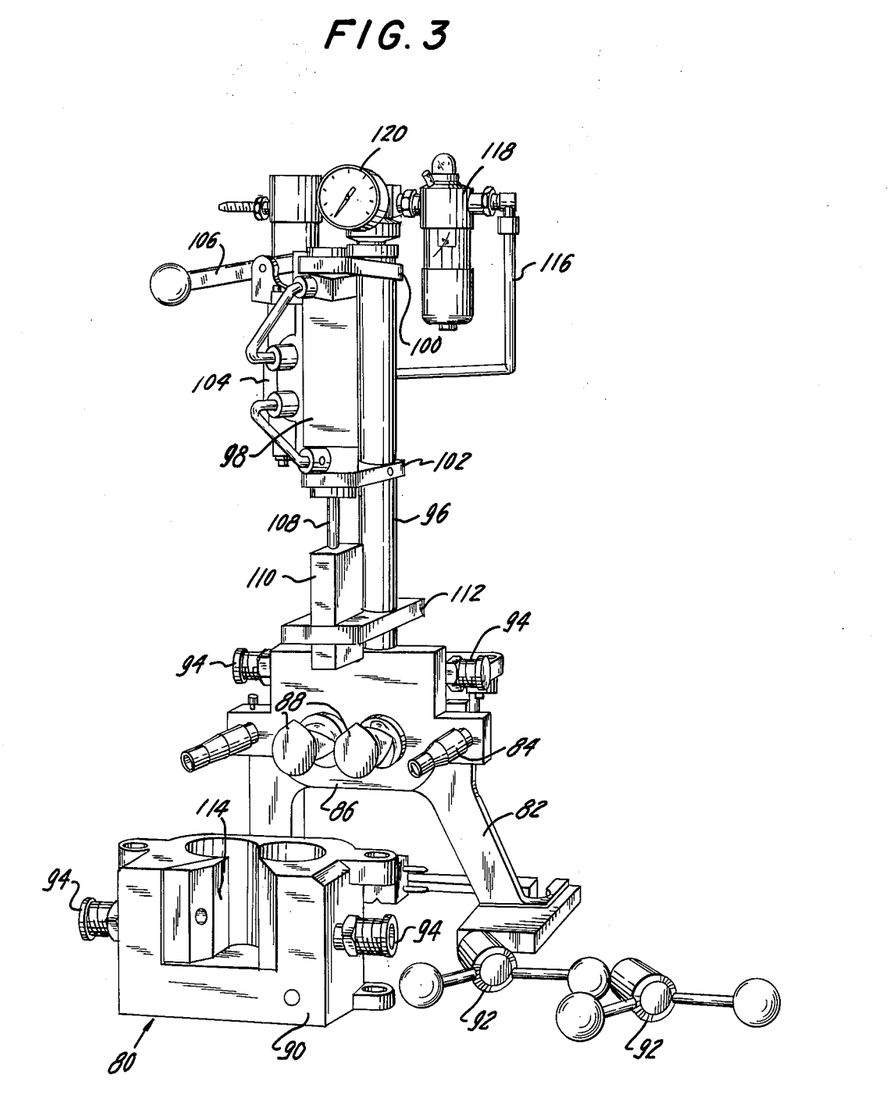
FIG. 3 is a perspective view of the mixing head of FIG. 2 shown as partially disassembled so as to more clearly show the mixer geometry.

In the mixing head shown, an air actuated ram is in cooperative functional relationship therewith. A ram support 96 is attached to and extends vertically from measuring head support 82 for positioning the ram over the throat of the mixer measuring head. On the ram support an air cylinder 98 is held by upper and lower cylinder support plates 100 and 102, respectively, with associated air cylinder operator 104 manual operation level 106. In the operate position, the operator 104 is arranged to cause the air piston head (not shown) to move downwardly causing the output shaft 108 to carry the ram head 110 through ramhead guide 112 into throat 114 or the mixing bowl 90. The air cylinder is connected to compressed air supply line 116 through filter 118 and gage 120.

Figure 4:
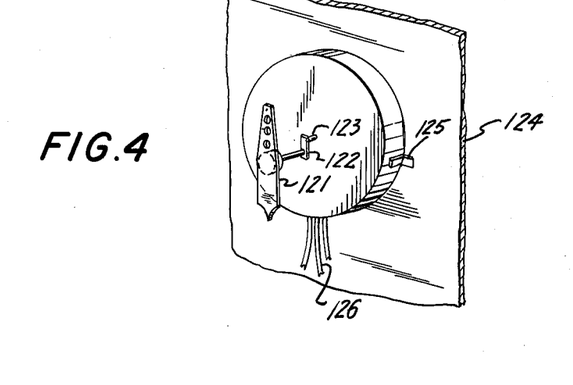
FIG. 4 is a partial cross sectional view of the scale indicator of FIG. 2 showing the variable potentiometer drive thereof.

Referring now to FIG. 4, a detail of the electronic/mechanical interface, namely, the linkage of potentiometer 68 to the scale indicator 51, is shown. The analog input of the torque integrator is produced by providing a variable resistance directly proportional to precent of full scale. The lower end of the indicator or shaft driver 121 of indicator movement 62 is coupled to the potentiometer driver 122 which in turn is mounted on potentiometer shaft 123. The potentiometer 68 is supported by the scale indicator case 124 by mounting brackets 125. The potentiometer leads 126 extending from the potentiometer 68 are used to impress a resistance upon a 5 vdc input signal and thereby provide an analog signal proportional to torque.

Figure 5:
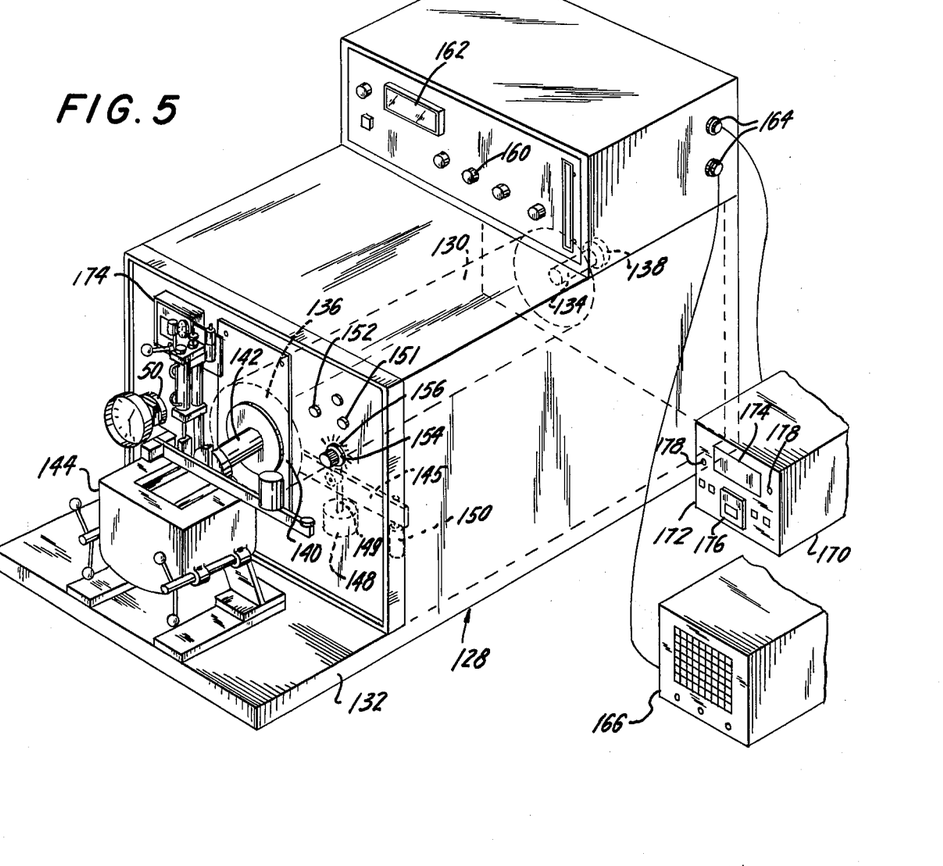
FIG. 5 is a perspective view showing the mechanical elements used to measure mixing torque for the electronic version of the second embodiment of the invention of FIG. 1.

The alternate embodiment to that of FIG. 2, above is the electronic torque rheometer 128 shown in FIG. 5. This embodiment described below has analogous elements numbered one hundred reference designators higher than that of the first embodiment. In other words, base plate 32 of the first embodiment is the analogous structure to base plate 132 of the second embodiment.

The electronic torque rheometer 128 is structured to include a dynamometer or drive 130 mounted on a base plate 132. The mounting arrangement provides for bearing housings 134 and 136 for retaining precision bearings 138 and 140, respectively. The precision bearing 138 accomodates one end of shaft 142 and the opposite end extends through bearing 140 for coupling to a driven unit 144. Medial to bearing 140 and driven unit 144 is mounted a load cell beam 146 connected in turn to load cell 148 through arm 149. The driven unit or measuring head 144 is similar to measuring head 44, discussed in detail above. The most commonly employed measuring head 144 is a miniature batch mixer utilizing the rotary power from dynamometer 130. Upon providing an output to the measuring head 144 a torque is experienced depending upon the materials being mixed, the time elapsed in the mixing cycle and numerous other factors including, but not limited to, mixer geometry. The torque rheometer 128 is provided with a mechanical stop arrangement 150 for limiting travel of arm 149. The scale zero is electrically suppressed through an attenuator structure 151 providing a variable resistance 152 controllable by selector switch 154 to any one of several detented stops 156. In place of providing as in the mechanical embodiment the lever arrangement 50 with an oil dashpot 60 that slows the rate of movement and oscillation of the mechanical linkage to the scale indicator, the electronic torque rheometer provides an electronic damping control 160. In the unit shown, the torque value is displayed on digital counter 162 and is structured to provide a millivolt output 164 for an external strip-chart recorder 166. Additionally, the output 164 is available for providing input to integrator unit 170. The panel 172 of integrator includes a digital readout meter 174 and a digital printer 176 for displaying integrated values.

Figure 6A:
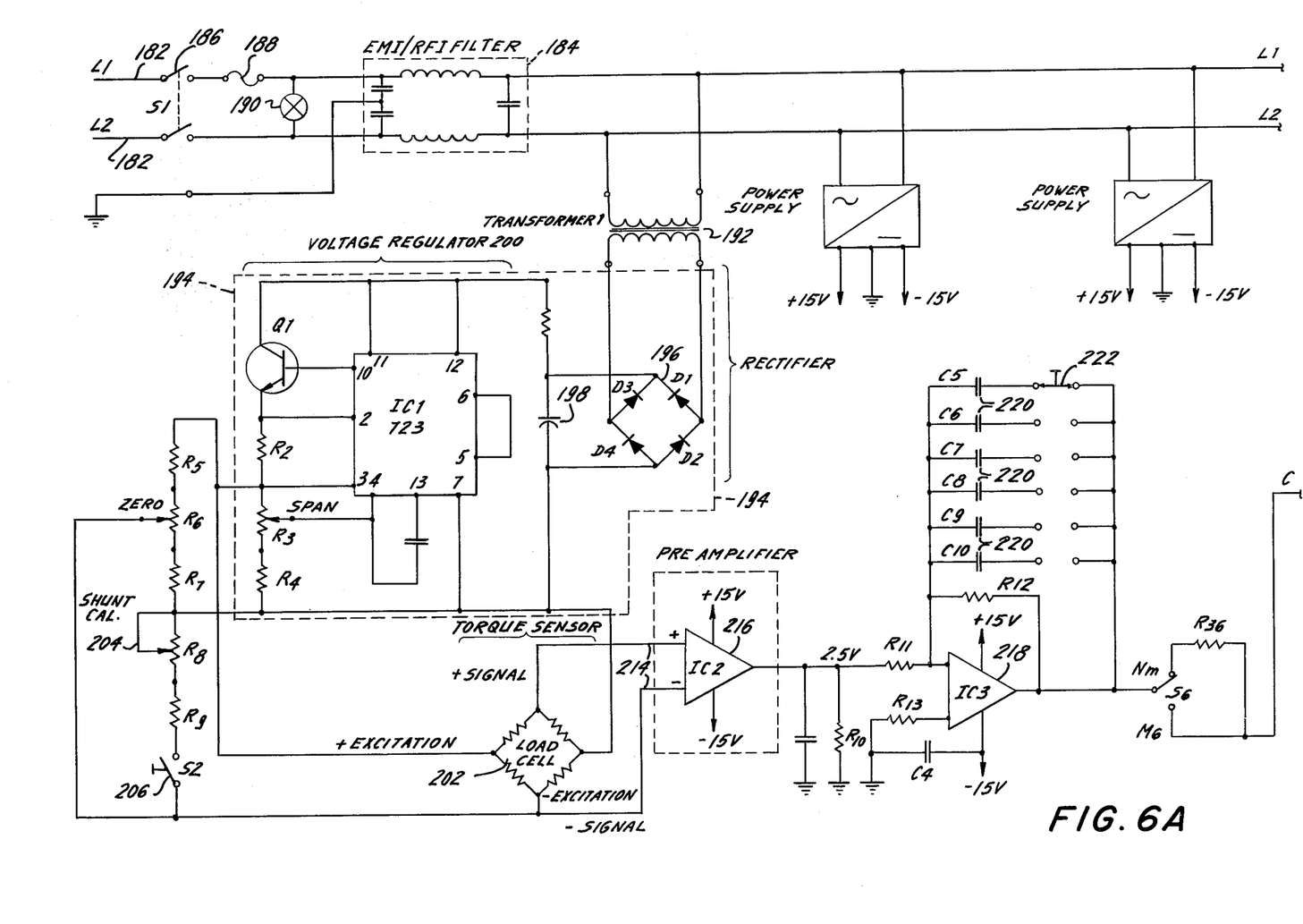
FIG. 6A and 6B is a schematic diagram of the torque rheometer of FIG. 5.
Figure 6B:
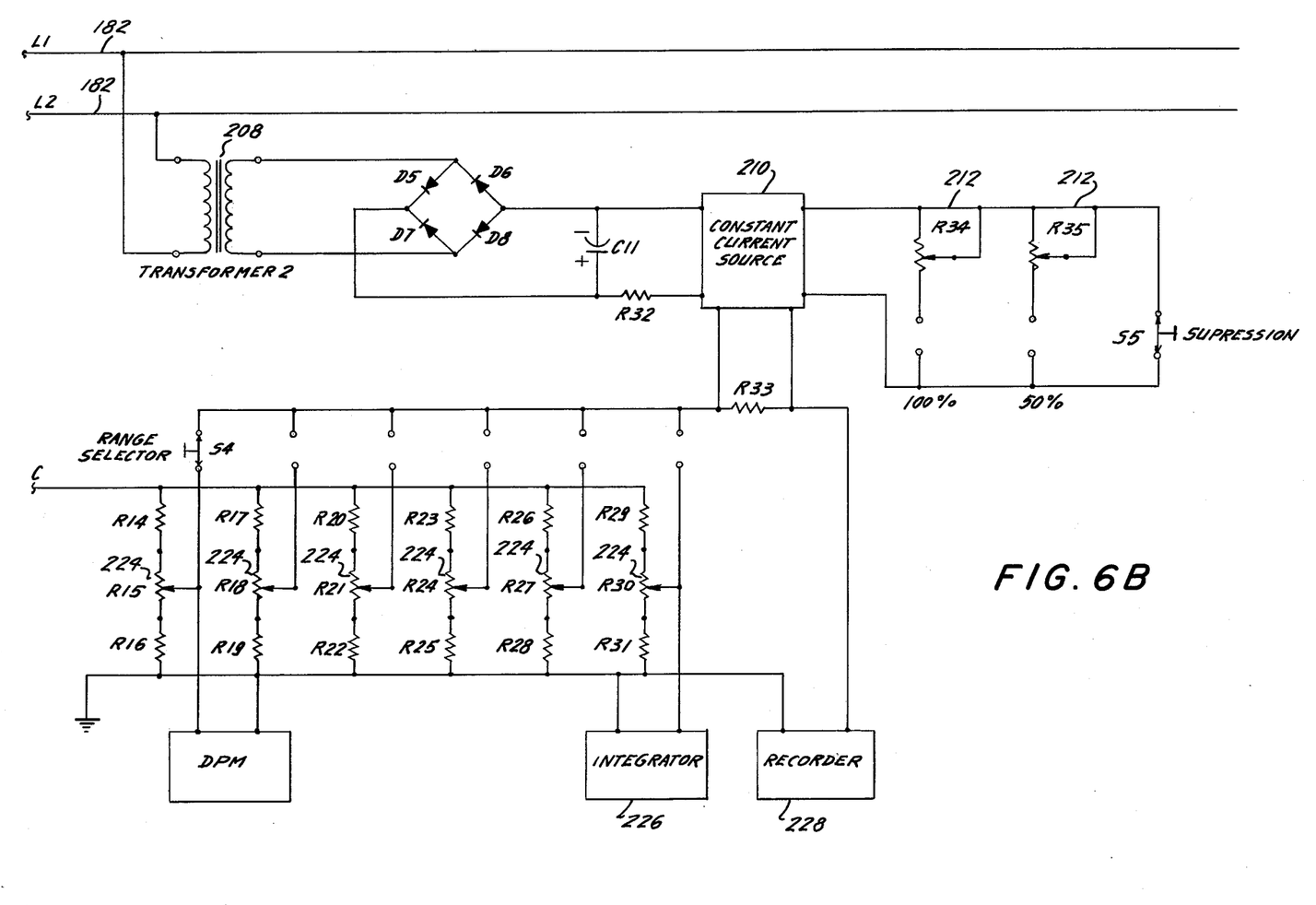

Referring now to FIG. 6A and 6B, a schematic diagram showing the torque rheometer is provided. The integrator shown is basically the same for both the electronic and mechanical embodiments of the present invention. Power from a-c source 180 is applied through power lines 182 through filter 184 by way of power switch 186. An in-line fuse 188 is connected to main a-c power lines 182. Beyond the fuse, an ON-OFF indicator lamp 190 is placed across the power lines. Lines 182 are also connected to the input windings of transformer 192 in a voltage regulated d-c power supply identified generally at 194. The output of transformer 192 is fed through rectifier network 196 and condenser 198 to voltage regulator 200. The power supply 194 supplies a very accurately regulated d-c output signal so as to facilitate accurate measurements within the system. While the schematic diagram shows the output power supply 194 being applied to a load cell of the electronic torque rheometer, the same basic circuitry is used in conjunction with the mechanical torque rheometer that uses the variable potentiometer. The major exceptions are that, in the integrator for the mechanical torque rheometer, resistances for zero suppression are selected to correspond with counterbalance weight 52 positioning and the damping is by way of an oil dashpot rather than the capacitance inducing circuit.

The output from power supply 194 is impressed upon load cell 202. For load cell adjustment in accordance with measuring head characteristics, a shunt calibration resistance 204 is provided which is insertable into and removable from the load cell circuit by test switch 206.

Lines 182 are also connected to the input windings of transformer 208 providing power for constant current source 210. Mounted adjacent the constant current source 210 are preload resistors 212 which provide the electronic equivalent of the counterbalancing weight in the mechanical unit. The load cell output signal lines 214 provide input to two stages of amplification at preamplifier 216 and amplifier 218. The output signal from preamplifier 216 is damped by selectively coupled capacitors 220 which are insertable into and removable from amplifier 218 circuitry by selector switch 222. The range of the output signal is attenuated by range selector resistors 224 and the output therefrom is available to torque indicator 226 and torque recorder 228.

Figure 7:
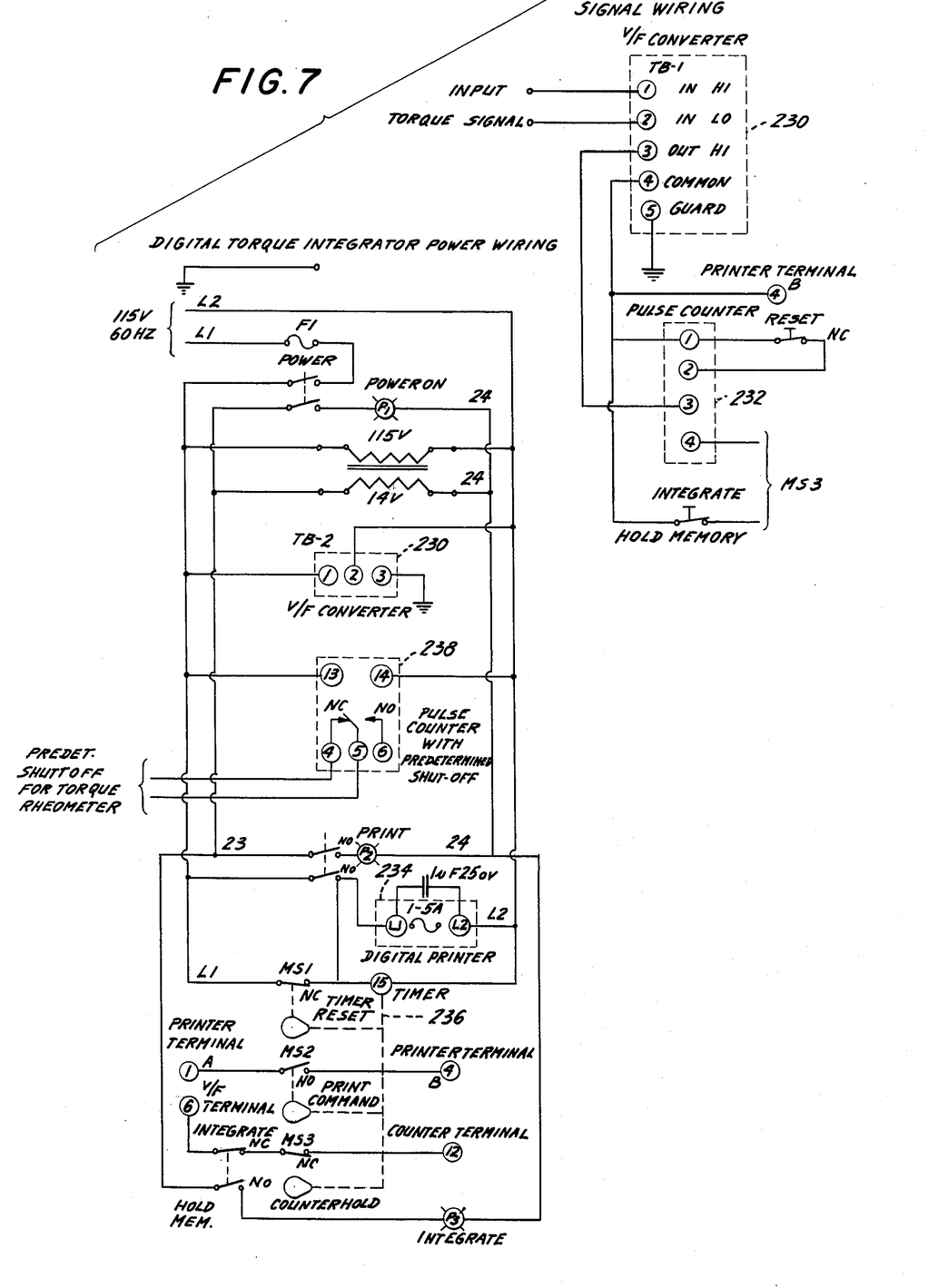
FIG. 7 is a schematic diagram of the integrator of FIG. 5.

Referring now to FIG. 7 the torque integrator wiring is shown. The torque signal from the torque rheometer of FIG. 6 is connected to the voltage-to-frequency converter 230 and from thence to pulse counter 232 and digital printer 234. The printer is in turn controlled by timer 236 to provide printed indication of accumulated count with a predetermined periodicity. The period in the instant case being 15 seconds. The mixing control system of this invention is shut off when the pulse counter reaches the present value of the pulse counter triggering the built-in relay 238 thereof.

In operation, the mixing control system determines work input by the integration of the area under the torque time curve. The torque rheometer provides an electrical signal proportional to torque which is electronically integrated with respect to time. The torque integrator provides a continuous digital readout of the area under the torque time-curve.

This readout can be used to calculate work input expressed in Joules, which can further be correlated with Watt-hour measurements from production machinery. In rotational mechanics, the basic equation governing the calculation of work input is:

$$2\pi \times \text{R.P.M.} = \int\int (\tau - t)\, dt$$

The digital torque integrator provides a continuous digital readout that is a measure of the value of the integral expressed in metergram minutes. This value is converted to work units by the factor $2\pi$ R.P.M. Since meter-grams are not proper units for work, the additional step of converting meter-grams to newton-meters is necessary to express meter-grams of work in joules. A joule is a unit of work and is equivalent to a force of 1 newton applied over a distance of 1 meter. As power is defined as work per unit time and a joule/sec is a watt, it is possible to compare integrated torque-time values direct to watt-hour measurements made on production machinery. The correlation is further enhanced if the work and watt-hour laboratory and production measurements are expressed on a per unit volume basis; i.e., joules/cm$^3$ or megajoules/M$^3$. In the present invention, the torque rheometer thereof provides an analog signal proportional to torque as measured by reaction torque of a dynamometer suspended between precision bearings. The torque is sensed and converted into a suitable electrical signal by a force transducer and suitable electronic signal conditioning device. The output signal is proportional to absolute torque and the maximum value is determined by the horse power and measuring range of the torque rheometer. For this discussion, an analog signal of O-5VDC corresponds to a torque range of 0–10,000 meter grams. The analog signal is fed directly into a high impedance voltage to frequency converter, which in turn generates a square-wave pulse whose frequency is variable in proportion to input. Calibration is adjustable, and in this example, the output of the converter is linearly related to the analog input. A 5-volt input to the V/F converter produces and output of 166.66 hz (10,000 counts/minute). Thus, each count is equivalent to 1 meter-gram-minute. The frequency output is fed into a pulse counter that continuously accumulates and displays the pulse generated by the frequency output of the converter. The counter incorporates a memory function, whereby the display can be frozen while it continues to internally accumulate pulses. When switched out of the memory mode, the display will automatically update. The counter provides an Binary Coded Decimal output which is interfaced with a data acquisition system (printer). The display of the counter is frozen while the printer interrogates the display (BCD), at pre-selected time intervals.

Although the invention has been described with specific reference to application to a laboratory-scale torque rheometer employing an apparatus known as a Banbury-type measuring head and a PVC mixture, it will be apparent that the principles of the invention may be employed with other elastomeric materials, including other plastics, and rubber, and with mixing or processing equipment, other than of the Banbury type. While specific embodiments of the invention presently considered to be the best mode have been disclosed in detail, it is to be understood that this is for the purpose of illustrating the invention, and should not be construed as necessarily limiting the scope of the invention, as it is apparent that many changes can be made to suit the disclosed structures to particular applications by those skilled in the art.

What is claimed is:

1. A mixing control system for elastomeric materials comprising:
   a mixer housing forming a mixing chamber therein for receiving said elastomeric materials
   at least one rotatable mixing means in the chamber;
   a dynamometer coupled to and driving said rotatable mixing means;
   torque sensing means for detecting torque exerted by the mixing means; said sensing means providing a torque signal level for controlling said mixing means;
   voltage-to-frequency conversion means for processing said signal level and for converting said signal level into a pulse signal in which the pulse frequency varies in correspondence to the amplitude of the signal level;
   pulse counting means for continuously and cumulatively counting the pulses of said pulse signal;
   display means for displaying the count of said pulse counting means as the value of the integral of said signal level with respect to time; and,
   control responsive means automatically responsive to a predetermined integrated value of said display means for controlling the total mixing energy input to the mixing control system.

2. A mixing control system as described in claim 1 wherein said torque sensing means comprises
   a scale indicator having a scale movement and a readout in units of torque
   a balanced beam attached to said dynamometer, said beam transmitting a force proportional to torque;
   a plurality of lever arms extending from said balanced beam to said scale indicator;
   variable resistance means for conditioning a d-c signal to provide said signal level proportional to torque, said variable resistance means mounted on said scale indicator and responsive to changes in readout thereof.

3. A mixing control system as described in claim 2 wherein said plurality of lever arms includes counterbalancing means for zero suppression of the scale of said scale indicator, said counterbalancing means adjustable to a discrete series of preselected settings.

4. A mixing control system as described in claim 3 wherein said torque sensing means further comprises
   a strip-chart recorder including a graphic chart thereof advanceable at a constant rate;
   pen arm means for linking said scale movement at one end thereof to said strip chart recorder.

5. A mixing control system as described in claim 4 wherein said integrator means provides a value of work input by integrating to find the area of said torque curve.

6. A mixing control system as described in claim 5 wherein said voltage-to-frequency conversion means includes
   a plurality of resistors insertable into and removable from circuitry for preconditioning said signal level to simulate said zero suppression of the scale.

7. A mixing control system as described in claim 6 wherein said integrator means includes a digital display of value accumulated.

8. A mixing control system as described in claim 7 wherein said digital display includes a counter arrest mechanism for stopping counter motion while continuing counter accumulation.

9. A mixing control system as described in claim 1 wherein said torque sensing means comprises
   a digital torquemeter having a readout in units of torque;
   a balancing beam attached to said dynamometer, said beam transmitting a fora proportional to torque;

a load cell attached to and functionally cooperative with said balanced beam for providing said signal level to said mixing control system.

10. A mixing control system as described in claim 9 wherein said signal level from said load cell is attenuated by loading resistors for zero suppression.

11. A mixing control system as described in claim 10 wherein said signal level from said load cell is connected to a variable capacitance circuit means for damping of oscillations of said signal level.

12. A mixing control system as described in claim 11 wherein said torque sensing means further comprises d-c milivolt signal means for strip-chart recording torque with respect to time.

13. A mixing control system as described in claim 12 wherein said integrator means provides a value of work input by integrating to find the area of said torque curve.

14. A mixing control system as described in claim 13 wherein said integrator means includes a digital display of value accumulated.

15. A mixing control system as described in claim 14 wherein said digital display includes a counter arrest mechanism for stopping counter motion while continuing counter accumulation.

* * * * *